United States Patent
Dutta Choudhury et al.

(10) Patent No.: US 12,249,416 B2
(45) Date of Patent: Mar. 11, 2025

(54) SYSTEMS AND METHODS FOR PROTOCOL RECOMMENDATIONS IN MEDICAL IMAGING

(71) Applicant: GE Precision Healthcare LLC, Wauwatosa, WI (US)

(72) Inventors: Arindam Dutta Choudhury, Bengaluru (IN); Vignesh Doraiswamy, Waukesha, WI (US); Yaxi Shen, Waukesha, WI (US); Ravi Raj Singh, Bengaluru (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 650 days.

(21) Appl. No.: 17/454,970

(22) Filed: Nov. 15, 2021

(65) Prior Publication Data
US 2023/0154594 A1 May 18, 2023

(51) Int. Cl.
G16H 30/40 (2018.01)
G16H 10/60 (2018.01)
G16H 30/20 (2018.01)
G16H 50/20 (2018.01)

(52) U.S. Cl.
CPC .......... *G16H 30/40* (2018.01); *G16H 10/60* (2018.01); *G16H 30/20* (2018.01); *G16H 50/20* (2018.01)

(58) Field of Classification Search
CPC ........ G16H 30/40; G16H 10/60; G16H 30/20; G16H 50/20
See application file for complete search history.

(56) References Cited

U.S. PATENT DOCUMENTS

| | | | |
|---|---|---|---|
| 7,613,835 B2 | 11/2009 | Sato | |
| 9,524,327 B2 | 12/2016 | Kang et al. | |
| 2005/0121505 A1* | 6/2005 | Metz | G16H 10/65 700/214 |
| 2012/0271840 A1* | 10/2012 | Vosniak | G16H 50/20 707/E17.014 |
| 2013/0090946 A1* | 4/2013 | Foo | G16H 10/65 705/3 |
| 2013/0311472 A1* | 11/2013 | Cohen-Solal | G16H 30/20 707/737 |
| 2015/0085971 A1* | 3/2015 | Braun | A61B 6/54 378/8 |
| 2016/0171163 A1* | 6/2016 | Hussam | G16H 10/60 705/3 |
| 2018/0144822 A1* | 5/2018 | Guendel | G06N 20/20 |
| 2018/0144823 A1* | 5/2018 | Raman | H04L 67/55 |
| 2018/0330818 A1* | 11/2018 | Hsieh | G16H 30/40 |

(Continued)

FOREIGN PATENT DOCUMENTS

WO 2021108398 A1 6/2021

*Primary Examiner* — David Bilodeau
(74) *Attorney, Agent, or Firm* — McCoy Russell LLP (57) ABSTRACT

Methods and systems are provided for automated protocol recommendation and selection in a medical imaging system. In one example, a method for the medical imaging system may include receiving an imaging order for an operator requesting an exam be performed on a patient using the medical imaging system, recommending a scan protocol for conducting the exam based on historical selections data for the operator and patient demographic data for the patient, and outputting the recommended scan protocol for display on a display device and/or automatically executing the recommended scan protocol.

19 Claims, 5 Drawing Sheets

(56) References Cited

U.S. PATENT DOCUMENTS

| | | | |
|---|---|---|---|
| 2019/0108903 A1* | 4/2019 | Kalafut | G06Q 10/10 |
| 2019/0131011 A1* | 5/2019 | Sevenster | G16H 30/20 |
| 2020/0380124 A1* | 12/2020 | Yavuz | G06N 7/01 |
| 2021/0193331 A1* | 6/2021 | Raman | G16H 40/40 |

* cited by examiner

SYSTEMS AND METHODS FOR PROTOCOL RECOMMENDATIONS IN MEDICAL IMAGING

FIELD

Embodiments of the subject matter disclosed herein relate to medical imaging systems, and more particularly to systems and methods for automating recommendation of medical imaging scan protocols.

BACKGROUND

Medical imaging may be performed to diagnose or rule out a patient condition. Typically, a clinician such as a physician may order a medical imaging exam using generic terminology that is translated to specific machine settings (referred to as a scan protocol) via a two-layered process performed manually by multiple parties, such as a radiologist and an imaging technologist.

BRIEF DESCRIPTION

In one embodiment, a method for a medical imaging system may include receiving an imaging order for an operator requesting an exam be performed on a patient using the medical imaging system, recommending a scan protocol for conducting the exam based on historical selections data for the operator and patient demographic data for the patient, and outputting the recommended scan protocol for display on a display device and/or automatically executing the recommended scan protocol.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
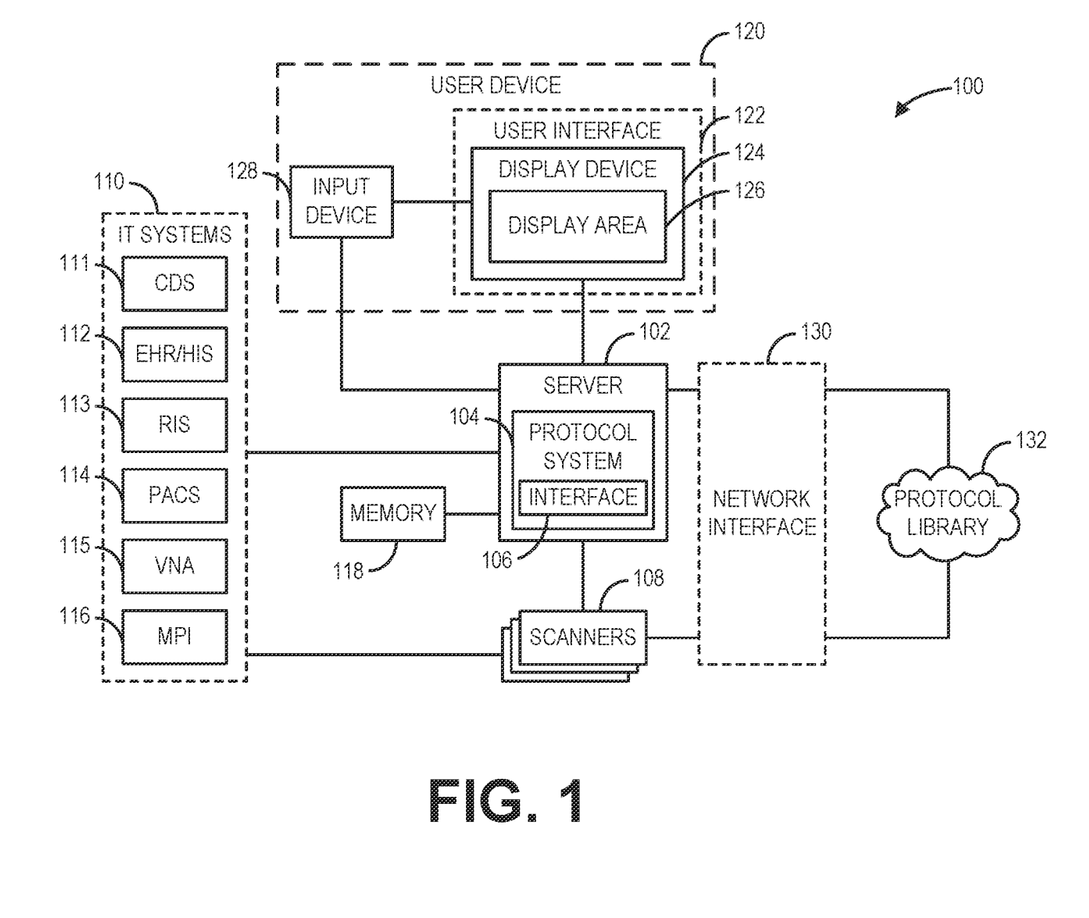
FIG. 1 shows a schematic block diagram of an exemplary medical imaging system, according to an embodiment.
Figure 2:
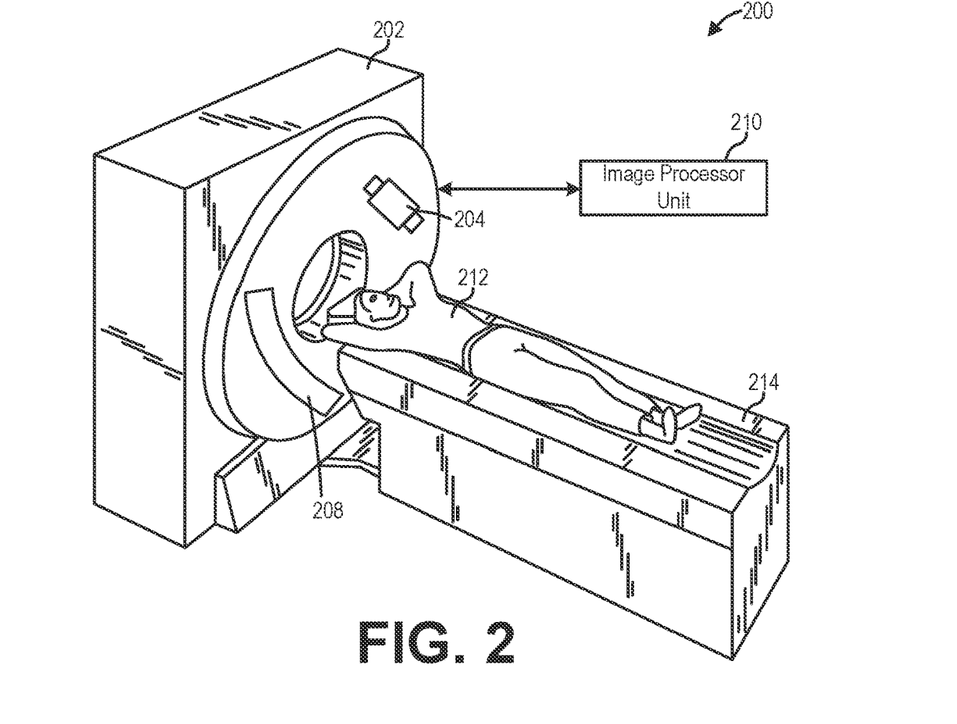
FIG. 2 shows a pictorial view of an exemplary computed tomography (CT) imaging system, according to an exemplary embodiment.
Figure 3:
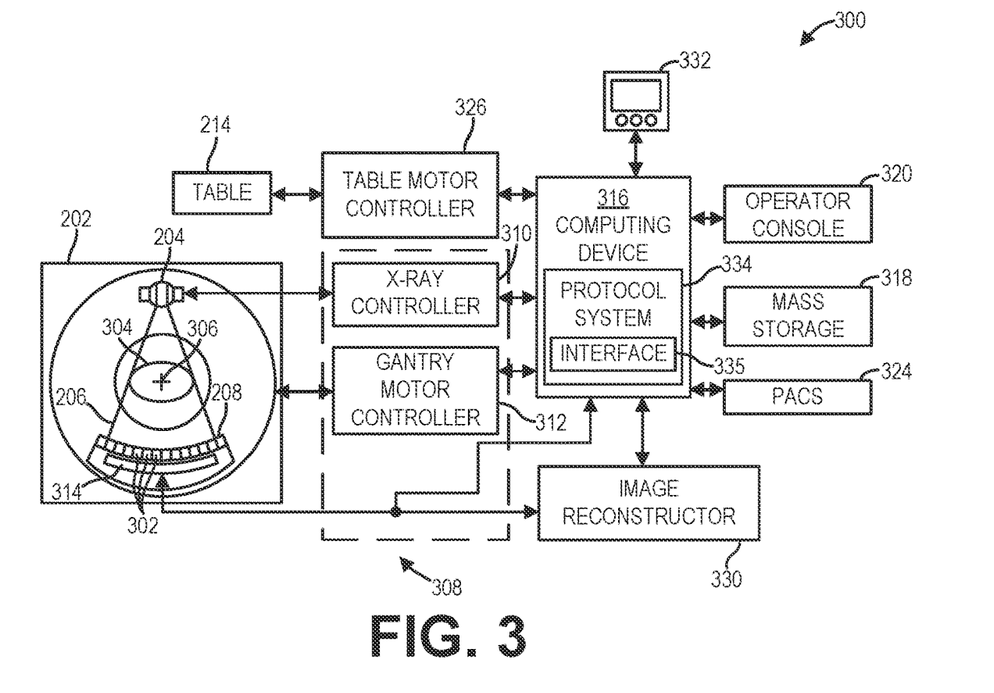
FIG. 3 shows a schematic block diagram of the exemplary CT imaging system, according to an exemplary embodiment.
Figure 4:
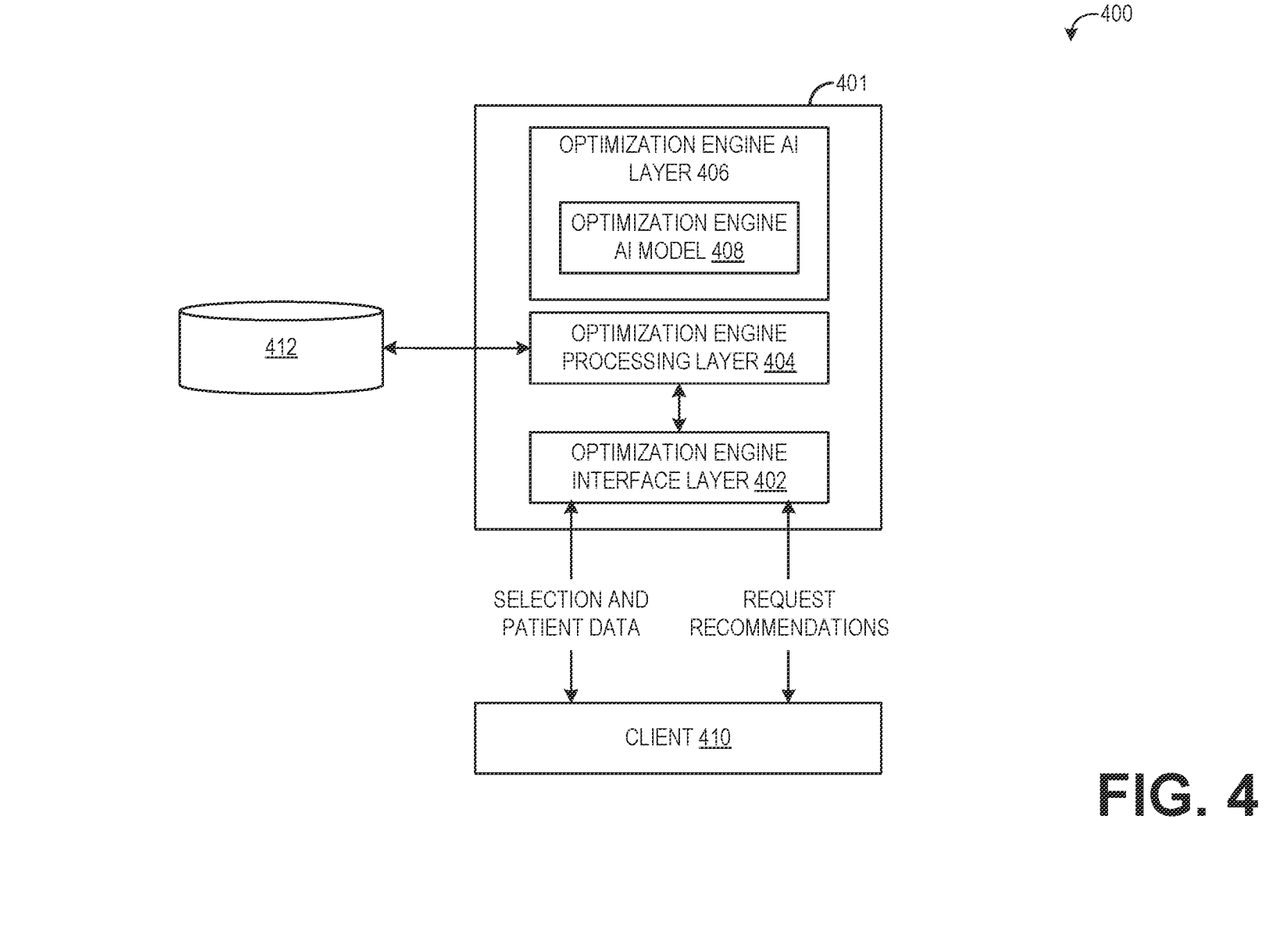
FIG. 4 shows a schematic diagram illustrating an example system architecture for providing scan protocol recommendations via a recommendation model.
Figure 5:
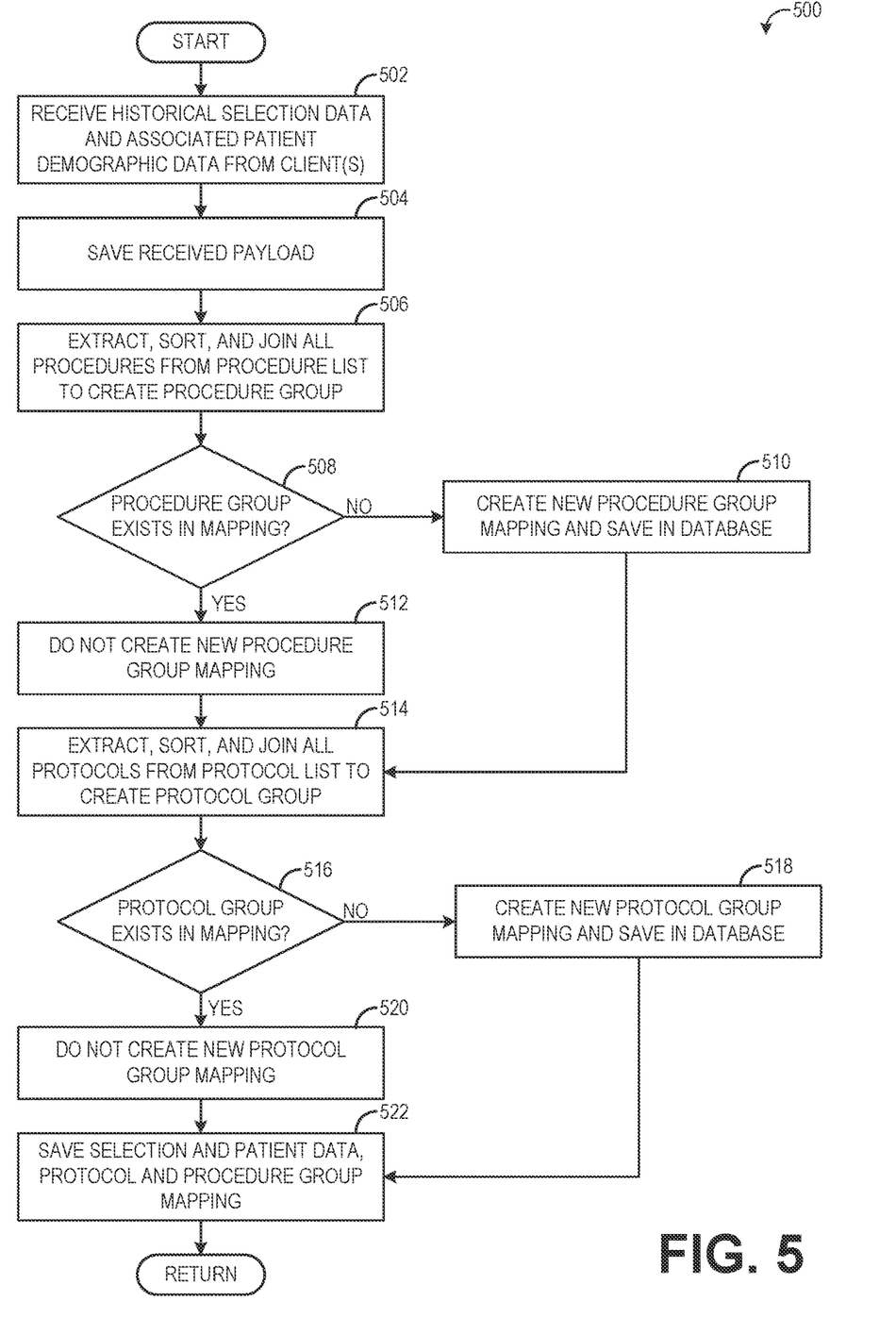
FIG. 5 is a flow chart illustrating an example method for data collection and training of the recommendation model.
Figure 6:
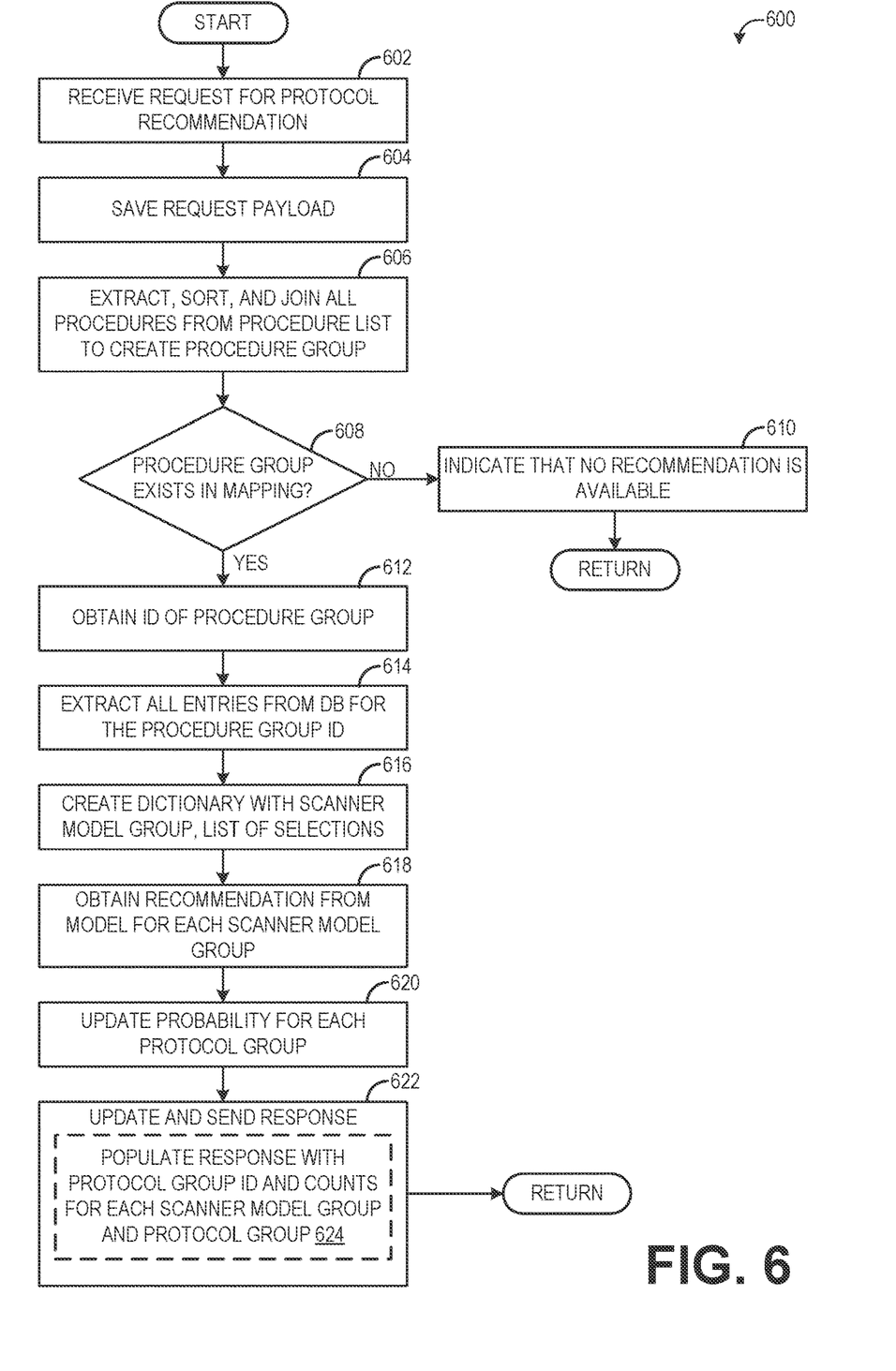
FIG. 6 is a flow chart illustrating an example method for recommending scan protocols via the recommendation model.

The following description relates to various embodiments of medical imaging systems, and automated protocoling recommendations therefor. One such medical imaging system employing an intelligent automated protocoling recommendation system is depicted in FIG. 1, including a plurality of scanners (e.g., medical imaging systems), an example of which is shown in FIGS. 2 and 3. The intelligent automated protocoling recommendation system (also referred to herein as a recommendation system) may generate protocol recommendations based on adaptive learning paradigms as implementable on a system architecture, such as the exemplary system architecture of FIG. 4. Exemplary workflows for generating such protocol recommendations and initiating corresponding scan sessions are depicted in FIGS. 5 and 6.

Referring now to FIG. 1, a block diagram of an example system 100 is depicted according to an embodiment. In the illustrated embodiment, the system 100 is a medical imaging system implementing multiple imaging modalities on respective scanners 108. It will be appreciated that embodiments set forth herein may implement any number of scanners 108. It will be understood that still other embodiments may not actively acquire medical images. Instead, such embodiments may retrieve images or imaging data that was previously acquired by an imaging system and analyze the imaging data as set forth herein.

As shown, the system 100 may include multiple components. The components may be coupled to one another to form a single structure, may be separate but located within a common room, or may be remotely located with respect to one another. For example, one or more of the modules described herein may operate in a data server that has a distinct and remote location with respect to other components of the system 100, such as at least one of the scanners 108 and a user device 120. Optionally, the system 100 may be a unitary system that is capable of being moved (e.g., portably) from room to room. For example, the system 100 may include wheels or be transported on a cart.

In the illustrated embodiment, a server 102 may be a computing device configured to interface with other components of the system 100 (e.g., via an interface 106). As such, the server 102 may be configured to control operation of the system 100. In embodiments described herein, the server 102 may implement an intelligent automated protocoling recommendation system 104 (referred to as a recommendation system 104) configured to automatically recommend scan protocols based on received medical data. Further, the recommendation system 104 may be operable to translate the selected scan protocols to scan protocol executables for initiating a scan session at at least one of the scanners 108. In some embodiments, the recommendation system 104 may automatically recommend, select, and translate the scan protocols for initiating the scan session upon receiving an input including the medical data (e.g., a scan order, clinical indications, patient medical histories, prior exam images, prior reports, etc.). In additional or alternative embodiments, the recommendation system 104 may recommend and display scan protocols (e.g., at a display area 126 of a display device 124) and may then await confirmation from one or more medical professionals for selection and/or translation of the recommended protocols. The recommendation system 104 may accordingly include the interface 106 for receiving and transmitting the medical data and the recommended scan protocols or scan protocol executables.

In various embodiments, the server 102 may take the form of a mainframe computer, server computer, desktop computer, laptop computer, tablet device, network computing device, mobile computing device, mobile communication device, etc. In one embodiment, the server 102 may take the form of an edge device for interfacing between the user device 120, the scanners 108, information technology (IT) systems 110, a master protocol library 132, etc.

The recommendation system 104 may take the form of a logic subsystem including one or more physical devices configured to execute one or more instructions. For example, the recommendation system 104 may be configured to execute one or more instructions that are part of one or more applications services, programs, routines, libraries, objects, components, data structures, or other logical constructs. Such instructions may be implemented to perform a task, implement a data type, transform a state of one or more devices, or otherwise arrive at a desired result.

The recommendation system 104 may include one or more processors configured to execute software instructions. In additional or alternative embodiments, the recommendation system 104 may include one or more hardware or firmware logic machines configured to execute hardware or firmware instructions. The one or more processors may be single- or multi-core, and programs executed thereon may be configured for serial or parallel or distributed processing. The recommendation system 104 may optionally include individual components distributed throughout two or more devices corresponding to the server 102, where the two or more devices may be remotely located and/or configured for coordinated processing. Further, one or more aspects of the recommendation system 104 may be virtualized and executed by remotely accessible networked computing device configured in a cloud computing configuration.

The server 102 may be in communication with a memory 118, either included in a computing device corresponding to the server 102 or may be a separate device communicably coupled to the server 102. Accordingly, the memory 118 may include removable media and/or built-in devices. Specifically, the memory 118 may include one or more physical, non-transitory devices configured to hold data and/or instructions executable by the recommendation system 104 to implement the herein described methods. When such methods are implemented, a state of the memory 118 may be transformed (for example, to hold different, or altered, data).

In some embodiments, the memory 118 may include optical memory (e.g., configured to read compact discs (CDs), digital versatile discs (DVDs), high-definition DVDs (HD-DVDs), Blu-ray discs, etc.), magnetic memory devices (e.g., hard drive disks, floppy disk drives, tape drives, magnetoresistive random-access memory (MRAM), etc.), and the like. In some embodiments, the recommendation system 104 and the memory 118 may be integrated into one or more common devices, such as an application-specific integrated circuit or a system on a chip. It will be appreciated that the memory 118 may be a non-transitory storage medium.

The server 102 may further be communicably coupled with IT systems 110, where the IT systems 110 may include one or more clinical decision support systems (CDS) 111, electronic health or medical records and/or hospital information systems (EHR/HIS) 112, radiological information systems (RIS) 113, picture archiving and communications systems (PACS) 114, vendor neutral archives (VNA) 115, master patient indices (MPI) 116, etc. Each of the IT systems 110 may provide the server 102 with medical data relevant to a scan order queried at the user device 120. As an example, medical data corresponding to the scan order (e.g., clinical indications, patient medical histories, patient allergies, etc.) may be selected by a medical professional operating the user device 120, and the medical data may be retrieved from the EHR/HIS 112. As another example, upon receiving the scan order, the recommendation system 104 may enter free text in the EHR/HIS 112 or select further medical data (e.g., prior reports, modality worklists, prior exam images, etc.) from the RIS 113 and/or the PACS 114. In some embodiments, the scanners 108 may also be communicably coupled to the IT systems 110, and may similarly receive medical data therefrom (for example, the scanners 108 may receive modality worklists from the RIS 113).

The server 102 and the scanners 108 may be communicably coupled to one another. In some embodiments, each of the scanners 108 may correspond to a different imaging modality (e.g., x-ray, magnetic resonance (MR), ultrasound (US), CT, positron emission tomography (PET), single-photon emission CT (SPECT), and combinations thereof, e.g., multi-modality imaging, such as PET/CT, PET/MR, SPECT/CT, etc.). In other embodiments, each of the scanners 108 may correspond to the same imaging modality, whereby each of the scanners 108 may be located in a separate room (e.g., in a hospital) or in separate facilities (e.g., hospitals) altogether. In still other embodiments not depicted at FIG. 1, the system 100 may include only one scanner 108 directed to a single imaging modality (e.g., such as in the CT imaging system as described below with reference to FIGS. 2 and 3).

A master protocol library 132 may be stored on a longer-term storage device or network, such as a cloud-based computing device or server. However, it will be appreciated that the master protocol library 132 may be stored on any known data storage medium, for example, a permanent storage medium, removable storage medium, and the like. As such, it will be appreciated that the master protocol library 132 may be stored on a non-transitory storage medium. It will be appreciated that the scanners 108 and/or remote devices (not shown) may have access to the master protocol library 132, such that the scanners 108 and/or remote devices may be enabled to periodically update the master protocol library 132 by adding, removing, substituting, or otherwise altering scan protocols stored on the master protocol library 132 (for example, in the case of the scanners 108, the periodic updating may be based on newly received and executed scan protocols).

Each of the server 102 and the scanners 108 may be communicably coupled to the master protocol library 132. In embodiments wherein the server 102 and/or the scanners 108 remotely access the master protocol library 132 over a network, communications therebetween may occur across a network interface 130 (e.g., a firewall). For example, the server 102 and/or the scanners 108 may communicate with and/or across the network in a wired and/or wireless manner via the network interface 130. The network may be a wireless telephone network, a wireless local area network, a wired local area network, a wireless wide area network, a wired wide area network, etc. In some embodiments, the network interface 130 may allow messages to be sent and/or received to and/or from other devices or entities, such as the master protocol library 132, via the network (e.g., the public Internet). In some embodiments, the network may be regarded as a private network connection and may include, for example, a virtual private network or an encryption or other security mechanism employed over the public Internet.

The recommendation system 104 may recommend scan protocols to be executed by the at least one of the scanners 108. The at least one of the scanners 108 may then receive the recommended scan protocols as executables from the server 102, whereby a scan session may be initiated. In some embodiments, a medical professional may instead manually query a scan protocol, which may be directly received by the at least one of the scanners 108 from the master protocol library 132, and the scan session may be initiated therefrom. It will be appreciated that when a scan protocol has been selected and executed, regardless of whether the scan protocol has been recommended by the recommendation system 104 or the scan protocol has been manually provided by the medical professionals, the recommendation system 104 may update a local protocol mapping library (e.g., on the memory 118) based on the selected and executed scan protocol. The local protocol mapping library may map protocols to procedures, such that when a scan order for a given procedure is received, the recommendation system 104 may identify suggested protocols based on the protocol to procedure mapping.

In operation, the server 102 may acquire medical data (e.g., from the IT systems 110) and imaging data (e.g., from the scanners 108), which may be translated for display to an operator or user (e.g., the medical professional) on the display device 124. As an example, the medical data may be transformed into and displayed at the display device 124 as a user-facing graphical and/or textual format, which may be standardized across all user devices 120 or may be particular to a given facility, department, profession, or individual user. As another example, the imaging data (e.g., three-dimensional (3D) volumetric data sets, two-dimensional (2D) imaging slices, etc.) may be used to generate one or more images at the server 102 or the user device 120, which may then be displayed to the operator or user at the display device 124.

In some embodiments, the server 102 may be communicably coupled to the display device 124 via a user interface 122 that enables an operator to control at least some operations of the system 100. The user interface 122 may include hardware, firmware, software, or a combination thereof that enables an individual (e.g., the operator) to directly or indirectly control operation of the system 100 and the various components thereof. As shown, the user interface 122 may include the display device 124, the display device 124 including the display area 126. In some embodiments, each of the server 102 and the user interface 122 may be operably connected to one or more user interface input devices 128, such as a physical keyboard, mouse, and/or touchpad. As an example, a touchpad may be configured to the server 102 and the display area 126, such that when a user moves a finger/glove/stylus across a face of the touchpad, a cursor atop a displayed medical record, image, etc. on the display device 124 may move in a corresponding manner.

In an exemplary embodiment, the display device 124 is a touch-sensitive display (e.g., touchscreen) which may detect a presence of a touch from the operator on the display area 126 and may also identify a location of the touch in the display area 126. The touch may be applied by, for example, at least one of the operator's hand, glove, stylus, or the like. As such, the touch-sensitive display may also be characterized as an input device that is configured to receive inputs from the operator (such as a queried medical procedure).

The display device 124 may communicate information from the server 102 to the operator by displaying the information to the operator. The display device 124 and/or the user interface 122 may also communicate audibly. The display device 124 may be configured to present information to the operator immediately before, during, and after the scan session. The information presented may include formatted medical records, images from one or more of the scanners 108, graphical elements, measurement graphics of displayed images, user-selectable elements, user settings, and other information (e.g., administrative information, other personal information of a patient, and the like).

As shown in FIG. 1, the user device 120 may include at least some of the components of the system 100 (e.g., the user interface 122, the display device 124, the display area 126, the input device 128, etc.). In some embodiments, the user device 120 may take the form of one or more of a mainframe computer, server computer, desktop computer, laptop computer, tablet device, network computing device, mobile computing device, mobile communication device, etc. In some embodiments, the user device 120 may be a personal mobile device interfacing with the server 102 via an application stored thereon. In other embodiments, the user device 120 may not be a single physical device, and the various components thereon may be associated with other aspects of the system 100. As an example, a single device may include the server 102, the user interface 122, the display device 124, the display area 126, and the input device 128. As another example, the user interface 122, the display device 124, the display area 126, and the input device 128 may be integrated with one of the scanners 108.

The server 102 or the user device 120 may implement an image-processing module which may receive imaging data from a given scanner 108 and then process the imaging data. For example, the image-processing module may process 3D volumetric imaging data to generate 2D image slices for displaying to the operator of the system 100. Similarly, the image processing module may process the imaging data to generate 3D renderings for displaying to the operator. It will be appreciated that acquired imaging data may be processed in real-time during a scanning session as signals are received at the given scanner 108. Additionally or alternatively, the imaging data may be stored temporarily in the memory 118 during the scanning session and processed in less than real-time in a live or off-line operation.

In addition to the image-processing module, the server 102 or the user device 120 may also include one or more of a graphics module, an initialization module, a tracking module, and an analysis module. The image-processing module, the graphics module, the initialization module, the tracking module, and the analysis module may coordinate with one another to present information to the operator during and after the scanning session. For example, the image-processing module may be configured to display an acquired image on the display device 124, and the graphics module may be configured to display designated graphics along with the displayed image, such as selectable icons and measurement parameters relating to the image.

A screen of the display area 126 of the display device 124 may be made up of a series, or matrix, of pixels which display the imaging data acquired with the scanners 108. The acquired imaging data may include one or more imaging parameters calculated for each pixel, or group of pixels (for example, a group of pixels assigned the same parameter value), of the display, where the one or more calculated image parameters may include one or more of an intensity, velocity (e.g., blood flow velocity), color flow velocity, texture, graininess, contractility, deformation, and rate of deformation value. The series of pixels may then make up the displayed image generated from the acquired imaging data.

In some embodiments, the server 102 or the memory 118 may include an adaptive learning module which includes one or more models (e.g., Gaussian model, deep neural network) and instructions for performing the adaptive learning functionalities described herein. For example, the recommendation system 104 may interface (e.g., via the interface 106) to the adaptive learning module such that the recommendation system may adaptively "learn" and recognize patterns in a series of executed scan protocols over time. As such, the recommendation system 104 may be configured to periodically update the adaptive learning module and/or data utilized by the adaptive learning module such that protocol recommendations may be made more consistent over time (in that medical expertise is accumulated over continued use of the system 100), thereby incrementally improving patient experience and health outcomes. As such, it will be appreciated that the recommendation system 104 and the IT systems 110 may update information related to medical scanning procedures in an asynchronous manner, allowing the recommendation system 104 to analyze and generate different, but related, data structures to those stored on the IT systems 110.

In general, numerous manual steps are included in a workflow for assigning a scanning protocol, initiating a scan session based on the scanning protocol, and acquiring images therefrom. When a patient arrives at a medical facility to diagnose a medical issue, an order may be placed by a clinician to a radiologist. The radiologist may then query data from multiple IT systems and may generate a radiologist-level scan protocol. The radiologist-level scan protocol may then be translated to a scanner-level scan protocol by a technologist. If a given technologist then has questions, the radiologist may be consulted for further review. In some examples, a given radiologist may have a high caseload or a given medical facility may be insufficiently staffed (e.g., may not employ an in-house radiologist), and a larger portion of protocol generation may be performed by less-experienced individuals. Further, experience may not only vary by individual or profession, but also by medical facility, such that there may exist geographic variability in scanning proficiency and consistency. Each of the above considerations may introduce variability into the workflow, thereby resulting in inconsistent treatment for substantially similar medical cases.

According to the embodiments disclosed herein, the above-described issues may be at least partly addressed by methods and systems for automated protocol recommendations for medical imaging modalities. For example, an intelligent automated protocol recommendation system may be in communication with one or more scanners, each scanner corresponding to any one of a plurality of medical imaging modalities. The recommendation system may automatically generate and assign protocol recommendations for a given order, and may then automatically select a scan protocol and a scanner therefor, or may await manual confirmation or selection of the scan protocol from the protocol recommendations by a medical professional (e.g., a scan technologist). The recommendation system may then update a local protocol mapping library based on the selection. In this way, the recommendation system may adaptively learn such that more consistent protocol recommendations may be generated for similar medical cases over time. That is, by reducing impediments to workflow efficiency, a consistency of medical imaging procedures may be improved across profession and geographic location, thereby improving patient experience and health outcomes.

As discussed with reference to FIG. 1, in some embodiments, the recommendation system (e.g., 104) may be configured to interface with a plurality of scanners (e.g., 108), such that the recommendation system may recommend scan protocols for more than one scanner and/or more than one imaging modality. However, in other embodiments, the recommendation system may be configured to interface with one or more scanners corresponding to only one imaging modality. That is, in some embodiments, the medical imaging system described herein may be directed to a specific imaging modality. In either example, FIGS. 2 and 3 provide an exemplary CT imaging system that may be coupled to or incorporating an exemplary embodiment of the recommendation system as described herein.

Referring now to FIG. 2, an exemplary system 200 configured for CT imaging is depicted. Specifically, the system 200 may be configured to image a subject 212 such as a patient, an inanimate object, one or more manufactured parts, and/or foreign objects such as dental implants, stents, and/or contrast agents present within the body. In one embodiment, the system 200 includes a gantry 202, which in turn, may further include at least one x-ray source 204 configured to project a beam of x-ray radiation 206 (see FIG. 3) for use in imaging the subject 212 laying on a table 214. Specifically, the x-ray source 204 may be configured to project the x-rays 206 towards a detector array 208 positioned on the opposite side of the gantry 202. Although FIG. 2 depicts only a single x-ray source 204, in certain embodiments, multiple x-ray sources and/or detectors may be employed to project a plurality of x-ray radiation beams 206 for acquiring projection data at different energy levels or angular orientations corresponding to the subject 212. In some embodiments, the x-ray source 204 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the system 200 further includes an image processor unit 210 configured to reconstruct images of a target volume of the subject 212 using an iterative or analytic image reconstruction method, or a combination of both. For example, the image processor unit 210 may use an analytic image reconstruction approach such as filtered backprojection (FBP) to reconstruct images of a target volume of the patient. As another example, the image processor unit 210 may use an iterative image reconstruction approach such as advanced statistical iterative reconstruction (ASIR) or model-based iterative reconstruction (MBIR), and the like, to reconstruct images of a target volume of the subject 212. In some examples, the image processor unit 210 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of radiation detectors. The intensity of the attenuated x-ray radiation beam received at the detector array is dependent upon the attenuation of an x-ray radiation beam by the object. Each detector element of the array produces a separate electrical signal that is a measurement of the x-ray beam attenuation at the detector location.

The attenuation measurements from all the detector elements are acquired separately to produce a transmission profile.

In some CT imaging systems, the x-ray source and the detector array are rotated with a gantry about the imaging plane and around the object to be imaged such that an angle at which the radiation beam intersects the object constantly changes. A group of x-ray radiation attenuation measurements, e.g., projection data, from the detector array at one angular position of the gantry is referred to as a "view." A "scan" of the object includes a set of views made at different angular positions, or view angles, during one revolution of the x-ray source and detector about the object. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, x-ray radiographic imaging, positron emission tomography (PET), or single-photon emission CT (SPECT) acquisition, and/or any other modality including modalities yet to be developed as well as combinations thereof in fused embodiments.

The projection data is processed to reconstruct an image that corresponds to one or more two-dimensional slices taken through the object or, in some examples where the projection data includes extended axial coverage, e.g., Z-axis illumination, a three-dimensional image volume of the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation maximization reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed axial coverage is acquired. Such a system generates a single helix from a cone-beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

Referring now to FIG. 3, an exemplary system 300 similar to the system 200 of FIG. 2 is depicted. That is, the system 300 may be a CT imaging system. In accordance with aspects of the present disclosure, the system 300 may be configured for imaging a subject 304 (e.g., the subject 212 of FIG. 2). In one embodiment, the system 300 includes the detector array 208 (see FIG. 2). The detector array 208 further includes a plurality of detector elements 302 that together sense the x-ray radiation beams 206 that pass through the subject 304 (such as a patient) to acquire corresponding projection data. Accordingly, in one embodiment, the detector array 208 is fabricated in a multi-slice configuration including the plurality of rows of cells or detector elements 302. In such a configuration, one or more additional rows of the detector elements 302 are arranged in a parallel configuration for acquiring the projection data.

In certain embodiments, the system 300 is configured to traverse different angular positions around the subject 304 for acquiring desired projection data. Accordingly, the gantry 202 and the components mounted thereon may be configured to rotate about a center of rotation 306 for acquiring the projection data, for example, at different energy levels. Alternatively, in embodiments where a projection angle relative to the subject 304 varies as a function of time, the mounted components may be configured to move along a general curve rather than along a segment of a circle.

As the x-ray source 204 and the detector array 208 rotate, the detector array 208 collects data of the attenuated x-ray beams. The data collected by the detector array 208 undergoes pre-processing and calibration to condition the data to represent the line integrals of the attenuation coefficients of the scanned subject 304. The processed data are commonly called projections.

The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the system 300 reveals internal features of the subject 304, expressed in the densities of two basis materials. The density image, or combinations of multiple density images, may be displayed to show these features. In traditional approaches to diagnosis of medical conditions, such as disease states, and more generally of medical events, a radiologist or physician would consider a hard copy or display of the density image, or combinations thereof, to discern characteristic features of interest. Such features might include lesions, sizes and shapes of particular anatomies or organs, and other features that would be discernable in the image based upon the skill and knowledge of the individual practitioner.

In one embodiment, the system 300 includes a control mechanism 308 to control movement of the components such as rotation of the gantry 202 and the operation of the x-ray source 204. In certain embodiments, the control mechanism 308 further includes an x-ray controller 310 configured to provide power and timing signals to the x-ray source 204. Additionally, the control mechanism 308 includes a gantry motor controller 312 configured to control a rotational speed and/or position of the gantry 202 based on imaging requirements.

In certain embodiments, the control mechanism 308 further includes a data acquisition system (DAS) 314 configured to sample analog data received from the detector elements 302 and convert the analog data to digital signals for subsequent processing. For photon-counting imaging systems, the DAS 314 downloads measured photon counts in one or more energy bins from detector array 208. The DAS 314 may be further configured to selectively aggregate analog data from a subset of the detector elements 302 into so-called macro-detectors, as described further herein. The data sampled and digitized by the DAS 314 is transmitted to a computer or computing device 316. In one example, the computing device 316 stores the data in a storage device or mass storage 318. The storage device 318, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 316 provides commands and parameters to one or more of the DAS 314, the x-ray controller 310, and the gantry motor controller 312 for controlling system operations such as data acquisition and/or processing. In certain embodiments, the computing device 316 controls system operations based on operator input. The computing device 316 receives the operator input, for example, including commands and/or scanning parameters via an operator console 320 operatively coupled to the computing device 316. The operator console 320 may include a keyboard (not shown) or a touchscreen to allow the operator to specify the commands and/or scanning parameters.

Although FIG. 3 illustrates only one operator console 320, more than one operator console may be coupled to the system 300, for example, for inputting or outputting system parameters, requesting examinations, plotting data, and/or viewing images. Further, in certain embodiments, the system 300 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the system 300 either includes, or is coupled to, a picture archiving and communications system (PACS) 324. In an exemplary implementation, the PACS 324 is further coupled to a remote system such as an RIS, EHR/HIS, and/or to an internal or external network (not shown) to allow operators at different locations to supply commands and parameters and/or gain access to the image data.

The computing device 316 uses the operator-supplied and/or system-defined commands and parameters to operate a table motor controller 326, which in turn, may control a table 214 which may be a motorized table. Specifically, the table motor controller 326 may move the table 214 for appropriately positioning the subject 304 in the gantry 202 for acquiring projection data corresponding to the target volume of the subject 304.

As previously noted, the DAS 314 samples and digitizes the projection data acquired by the detector elements 302. Subsequently, an image reconstructor 330 uses the sampled and digitized x-ray data to perform high-speed reconstruction. Although FIG. 3 illustrates the image reconstructor 330 as a separate entity, in certain embodiments, the image reconstructor 330 may form part of the computing device 316. Alternatively, the image reconstructor 330 may be absent from the system 300 and instead the computing device 316 may perform one or more functions of the image reconstructor 330. Moreover, the image reconstructor 330 may be located locally or remotely, and may be operatively connected to the system 300 using a wired or wireless network. For example, one embodiment may use computing resources in a cloud network cluster for the image reconstructor 330.

In one embodiment, the image reconstructor 330 stores the images reconstructed in the storage device 318, either via the computing device 316 as shown in FIG. 3 or via a direct connection (not shown). Alternatively, the image reconstructor 330 may transmit the reconstructed images to the computing device 316 for generating useful patient information for diagnosis and evaluation. In certain embodiments, the computing device 316 may transmit the reconstructed images and/or the patient information to a display or display device 332 communicatively coupled to the computing device 316 and/or the image reconstructor 330. In some embodiments, the reconstructed images may be transmitted from the computing device 316 or the image reconstructor 330 to the storage device 318 for short-term or long-term storage.

Some methods or processes described further herein may be stored as executable instructions in non-transitory memory on a computing device (or controller) in system 300. In one embodiment, image reconstructor 330 may include such executable instructions in non-transitory memory, and may apply the methods described herein to reconstruct an image from scanning data. In another embodiment, computing device 316 may include the instructions in non-transitory memory, and may apply the methods described herein, at least in part, to a reconstructed image after receiving the reconstructed image from image reconstructor 330. In yet another embodiment, the methods and processes described herein may be distributed across image reconstructor 330 and computing device 316.

In one embodiment, the display device 332 allows the operator to evaluate the imaged anatomy. The display device 332 may also allow the operator to select a volume of interest (VOI) and/or request patient information, for example, via a graphical user interface (GUI) for a subsequent scan or processing.

The computing device 316 may further store an intelligent automated protocol recommendation system 334 thereon, which may interface with various components of the system 300 via an interface 335. Accordingly, the recommendation system 334 may receive medical data from the PACS 324 or from a remote device storing another IT system (e.g., a CDS, EHR/HIS, RIS, VNA, MPI, etc.) and protocols from a master protocol library (not shown at FIG. 3), whereby the recommendation system 334 may automatically generate one or more protocol recommendations. A scan protocol may then be automatically selected from the one or more protocol recommendations, which may further be confirmed by an operator at the operator console 320. In some examples, the operator may instead enter a manual selection from the one or more protocol recommendations into the operator console 320 or may manually select another scan protocol entirely (e.g., not included in the one or more protocol recommendations). The recommendation system 334 may further interface (e.g., via the interface 335) to an adaptive learning module that may be periodically updated with feedback from the operator via the recommendation system 334 such that scan protocols may be more consistently recommended via adaptive learning paradigms.

It will be appreciated that the recommendation system 334 may be substantially similar to the recommendation system 104 of FIG. 1, excepting that the recommendation system 334 is specifically adapted to a single imaging modality (that is, CT imaging). However, it will further be appreciated that non-modality specific functionality of the recommendation system 334 may be substantially equivalent to that described above with reference to the recommendation system 104. Accordingly, further non-modality specific components of FIG. 1 may be added or substituted to the system 300 within the scope of the present disclosure.

As explained previously, protocoling encompasses the entire journey of mapping the order level protocol (procedure requested by the physician) to the radiologist level protocol and then eventually to the scanner level protocol. The whole process can be split into two phases—mapping the order level protocol to radiologist level protocol, performed by a radiologist, and choosing/selecting the scan level protocol based on the radiologist level protocol, performed by a technologist. Since the two phases are performed manually by two different professionals, certain issues/problems may arise at the protocoling stage. These issues may include undue time expenditure for both the radiologist and technologist in selecting the proper protocol and image quality, dose issues, and/or patient recall if an improper protocol is selected.

To address the above-described pain points, a protocol recommendation system is provided herein that uses an AI-based optimization engine to auto-generate protocol recommendations for a given imaging order. The architecture leverages patient demographic information and the historically encountered pattern of protocol selection to predict an accurate and reliable protocol suggestion. FIG. 4 shows an example system architecture 400 including a core optimization system 401 having an optimization engine interface layer 402, an optimization engine processing layer 404, and an optimization engine AI layer 406. The core optimization system 401 may generate protocol recommendations based on protocol selection historical data and patient information, as described herein. Thus, the core optimization system 401 may be a non-limiting example of the recommendation system 104.

The interface layer 402 (which may be a REST API based interface layer) acts as the interface for an optimization engine AI model 408 (which may be a non-limiting example of the adaptive learning module discussed above) and the processing layer 404 for any external client interactions. For example, FIG. 4 shows an external client 410, which may be a scanner, such as one of the scanners 108 of FIG. 1. In a non-limiting example, the external client 410 may be a CT imaging system, such as the CT system described above with respect to FIGS. 2-3. The client 410 may send requests for protocol recommendations, which the core optimization system 401 may respond to by identifying recommended protocols and sending the recommended protocols back to the client 410. Further, the client 410 may send selection data (e.g., which protocols were selected for a scan) to the core optimization system 401, which may be stored and used by the model 408 to recommend protocols. Further still, the client 410 may send patient data (e.g., age, body mass index (BMI)) to the core optimization system 401, which may be used by the model 408 for selecting a recommended protocol. The interface layer 402 may create a REST API-based wrapper around the core optimization system, enabling the capability to train or infer from the core optimization system. The processing layer 404 is responsible for ingesting the incoming training or inferencing request (e.g., the request for a recommendation or selection and patient data) received from the interface layer 402, processing the requests as per the workflow (which will be explained in more detail below with respect to FIGS. 5 and 6), fetching or saving necessary information from a database 412, and invoking the AI layer 406 in case of recommendation requests. The database 412 may store the selection data, patient data, protocol to procedure mapping, and/or protocols, which may be used by the model 408 to selected a recommended protocol. In some examples, the database 412 may store the selection data, patient data, and protocol to procedure mapping, and the protocols may be stored separately (e.g., on a master protocol library).

The AI layer 406 of the optimization engine loads and manages the AI model 408, which may be a machine-learning based model configured to select recommended protocols based on patient information (such as age and BMI) and prior protocol selections. In an example, the model 408 may be a Gaussian Naïve Bayes classifier which generates recommendations for the requested imaging orders. The statistical classifier treats the protocol recommendation as a classification problem.

The classification problem may include classifying a patient exam and recommending protocols based on the classifying. For example, given that, for a given procedure, n protocols have been used in the past, the core optimization system 401 treats each of these n protocols as individual classes. The problem then becomes: "Given a patient exam context, which class does this instance belong to?" This reframing allows for the use of machine learning statistical classification techniques to determine the appropriate protocol to use. As part of the post classification processing, a probability score may be associated to each class (protocol) to indicate the confidence associated with each recommended protocol.

The standard operation of the core optimization system 401 includes two distinct workflows, a learning workflow and an inferencing/recommendation workflow. An example learning workflow is shown in FIG. 5. The workflow captures the activity/process involved in accumulating the data that can be used to train the classifier model. An example inferencing/recommendation workflow is shown in FIG. 6. The workflow captures the activity/process involved in generating protocol recommendations from the classifier model.

FIG. 5 shows a method 500 for obtaining data for training a protocol recommendation model, such as model 408 of FIG. 4. Method 500 is described with regard to the systems and components of FIG. 1-4, though it should be appreciated that the method 500 may be implemented with other systems and components without departing from the scope of the present disclosure. Method 500 may be carried out according to instructions stored in non-transitory memory of a computing device, such as server 102 of FIG. 1 or core optimization system 401 of FIG. 4.

At 502, historical selection data and associated patient demographic data is received from one or more client devices, such as one or more of the scanners 108 and/or client 410, which may be imaging systems, such as CT imaging systems. The historical selection data and associated patient demographic data may be received by the interface layer of the core optimization system. In some examples, the historical selection data and associated patient demographic data may be pushed to the core optimization system from the client devices according to a synchronization process, though other mechanisms of receiving the historical selection data and associated patient demographic data are possible. At 504, the received payload (e.g., data) is saved, which may be performed by the processing layer of the core optimization system. The payload may include selection data and patient demographic data from one imaging scan that was performed. Thus, the remaining steps of method 500 may be specific to the payload and hence one scan, and it is to be appreciated that method 500 may be repeated for each payload that is received (e.g., for each scan that is performed). The historical selection data may include information relating to one or more scanning protocols that were executed on the scanner, and thus the historical selection data may include, for that scan, a procedure list of the scan (e.g., head CT), a protocol list of the scan with an identifier for each scanning protocol executed as part of the scan, such as a universally unique identifier (UUID), and the model of the scanner used to perform the scan. Further, in some examples, more than one procedure may be performed in the scan, and thus the procedure list may include more than one procedure (e.g., a CT angiography procedure and a CT perfusion procedure) and the protocol list may include two or more protocols. The patient demographic data may include demographic information about the patient that was imaged in the scan, such as age, height, weight, BMI, and/or sex.

At 506, all the procedures in the procedure list of the received data may be extracted, sorted, and joined to create a procedure group, which may be performed by the processing layer. As mentioned above, more than one procedure may be carried out during a scan, and the protocols that were carried out to perform the scan were selected (e.g., by a radiologist and/or technologist) based on each procedure. Thus, the model may be trained to select protocols based on all the procedures for a given scan, rather than each procedure independently. In particular, some procedures may be linked or interleaved in such a manner that independent protocol selection may be difficult or impossible. Thus, procedure groups may be created so that scan protocols can be classified by procedure group rather than by independent procedures. However, when only one procedure was performed in a scan, the procedure group may only include one procedure.

At 508, method 500 includes determining if the procedure group exists in a procedure group mapping of the database of the core optimization system (e.g., on the database 412). Each time the core optimization system receives historical selection data, a procedure group may be generated. Each unique procedure group may be assigned an identifier and saved in a procedure group mapping of the core optimization system database. The current procedure group may be evaluated and compared to the procedure groups in the procedure group mapping to determine if that procedure group has already been saved in the procedure group mapping. If the procedure group does not yet exist in the procedure group mapping of the database, method 500 proceeds to 510 to create a new procedure group mapping corresponding to the current procedure group and save the procedure group mapping in the database. Creating the procedure group mapping may include assigning a UUID to the procedure group. If the procedure group already exists in the procedure group mapping, method 500 proceeds to 512 and does not create a new procedure grouping mapping.

At 514, all protocols in the received protocol list are extracted, sorted, and joined to create a protocol group. Each protocol may be identified by a protocol ID (e.g., a UUID that uniquely identifies that protocol). In some examples, the specific parameters of each protocol may be saved in a protocol library (e.g., protocol library 132), where each unique protocol is assigned a protocol ID. In this way, the protocol information included in the payload may include the protocol IDs rather than specific protocol information, and only protocol IDs may be stored in the database. Similar to the procedure group, the grouping of protocols allows for the model to learn linkage of protocols that are frequently performed together, as some protocols may not be performed independently, or may be performed less efficiently if performed independently. However, when only one protocol was performed in a scan, the protocol group may only include one protocol. At 516, method 500 includes determining if the current protocol group already exists in a protocol group mapping of the database. If the protocol group does not yet exist, method 500 proceeds to 518 to create a new protocol group mapping and save the protocol group mapping in the database, which may include assigning a UUID to the protocol group mapping. If the protocol group already exists in the protocol group mapping, a new protocol group mapping is not created, as indicated at 520.

At 522, the selection data and patient data, protocol group mapping, and procedure group mapping are saved in a protocol-to-procedure mapping the database. For example, the protocol IDs, the patient demographic data, and the scanner model may be saved in the database, indexed by the protocol group mapping (e.g., the protocol group UUID) and the procedure group mapping (e.g., the procedure group UUID). The protocol-to-procedure mapping of the database may include protocol IDs for a plurality of protocols each indexed/mapped to one or more procedures/procedure groups. Method 500 then ends.

FIG. 6 shows a method 600 for generating protocol recommendations with a protocol recommendation model, such as model 408 of FIG. 4. Method 600 is described with regard to the systems and components of FIG. 1-4, though it should be appreciated that the method 600 may be implemented with other systems and components without departing from the scope of the present disclosure. Method 600 may be carried out according to instructions stored in non-transitory memory of a computing device, such as server 102 of FIG. 1 or core optimization system 401 of FIG. 4.

At 602, a request for a protocol recommendation is received. The request for the protocol recommendation may include a payload that includes the procedure(s) to be performed during the scan and patient information for the patient being imaged during the scan. The request for the protocol recommendation may be received by the interface layer of the core optimization system, which interfaces with the client device(s). The request for the protocol recommendation may be received from a scanner (e.g., one of the scanners 108 of FIG. 1) in response to a technologist entering input to the scanner requesting a protocol for a particular scan. The scan may be performed in response to a scan order (also referred to as an imaging order) being placed by a clinician (e.g., a doctor). The scan order may include patient information or information usable to obtain the patient information (e.g., patient age, sex, height, weight) and scan information, such as the imaging modality and a diagnostic goal/anatomical region of the scan (e.g., a CT head scan). In some examples, the request may be received from an EMR or an RIS in response to the scan order being placed (or in response to a radiologist level scan order being placed), rather than being received from the scanner.

At 604, the payload of the request is saved, which may be performed by the processing layer of the core optimization system. An example payload for a protocol recommendation request using REST API is shown below:

```
{
    "patientID"" "string",
    "procedureGroup:: [
        {
            "accesionNumber": "6235723",
            "procedureName": "CT HEAD"
        }
    ],
```

```
"demographics": {
    "patientAge": 4.2,
    "patientHeight": 1.4,
    "patientWeight": 66.3,
    "patientBmi": 22.4,
    "patientSex": "M"
}
}
```

At 606, the processing layer extracts, sorts, and joins all procedures in the procedure list of the payload to create a procedure group. For example, using the accession number and/or procedure name, a procedure group for "CT head" may be created in the above example. At 608, method 600 includes determining if the procedure group exists in the procedure group mapping of the database. As explained above with respect to FIG. 5, the protocols that are recommended are selected based on the procedure(s) being performed. If the procedure group of the ordered scan does not exist in the procedure group mapping of the database, method 600 proceeds to 610 to indicate that no scan protocol recommendation is available. Because the current procedure group is not in the database, specific protocol recommendations cannot be made by the model, and thus the protocol selection may be made manually by the technologist. In some examples, a notification may be sent to the client device that requested the protocol recommendation (e.g., the scanner) indicating that no recommendation is available. Method 600 then returns.

If the procedure group does exist in the procedure group mapping of the database, method 600 proceeds to 612 to obtain the procedure group ID of the current procedure group and, at 614, extract all entries from the database for the procedure group ID. As explained above with respect to FIG. 5, the information from the database that may be extracted at 614 includes the protocol ID(s) for the protocol (s) performed in the prior scans for the procedure group, as well as the scanner model for each scan and the patient information for each scan. At 616, a dictionary is created from the extracted entries. The dictionary may include the scanner model and list of protocols for each entry, formatted such that the <key, value> is <scanner model group, list of protocols>.

At 618, method 600 obtains one or more protocol recommendations from the recommendation model for each scanner model group. The recommendation model may be the model 408 and the recommendation may be generated by the AI layer of the core optimization system. The recommended protocols may include the protocol groups associated with the procedure group in the database, narrowed by patient demographics and scanner group model. In this way, recommended protocols may be obtained for each scanner model group based on prior protocols performed for the procedure group on each different scanner model.

To further narrow the recommended protocols and provide the end user (e.g., the technologist) with a confidence level of how closely associated the recommended protocols are with the procedure group, method 600 includes, at 620, updating the probability for each protocol group within each scanner model group. The recommendation model may be a statistical model configured to assign a probability to each potential protocol recommendation. In some examples, the recommendation model may be a Naive Bayes (NB) model, which includes a set of supervised learning algorithms based on applying the Bayes' theorem with the "naive" assumption of conditional independence between every pair of features given the value of the class variable. The prepared input to the recommendation model may include the protocol groups extracted from the database (e.g., the protocol groups associated with the procedure group) and a query vector, which may be the patient demographics such as age and patient size (e.g., body mass index).

Bayes' theorem states the following relationship, given class variable and dependent feature vector $x_i$ through $x_n$:

$$P(y \mid x_1, \ldots, x_n) = \frac{P(y)P(x_1, \ldots, x_n \mid y)}{P(x_1, \ldots, x_n)}$$

Since the distribution of the features is continuous, a Gaussian NB model may be used, where the likelihood of the features is assumed to be Gaussian:

$$P(x_i \mid y) = \frac{1}{\sqrt{2\pi\sigma_y^2}} \exp\left(-\frac{(x_i - \mu_y)^2}{2\sigma_y^2}\right)$$

In the above equations, y represents the protocol group and the feature vectors (e.g., $x_i$) are patient age and BMI. The parameters $\sigma_y$ and $\mu_y$ are estimated using maximum likelihood. The parameters represent the mean and variance of the feature (age and BMI) for a given protocol group y. In this way, the model undergoes learning via the calculation of probability density function using the data available for learning.

For the implementation of the model, the Gaussian NB module may be used to predict one or more protocol groups given the historical selection data and the patient demographics (e.g., which protocols were used in that procedure group in the past for patients of similar demographics). Each protocol group historically associated with the given procedure group is recommended along with a respective confidence score that represents the probability that, of the given data that is input into the model, the respective protocol group will be selected to carry out the scan. In instances where multiple protocol groups are recommended and/or some recommended protocol groups have low confidence scores, those protocol groups are still recommended, with the expectation that the client (e.g., scanner) can leverage the most appropriate protocol based on confidence scores associated with each protocol group. In some examples, at the scanner, a sort based on confidence scores may be performed to identify the protocol groups with the highest confidence scores, e.g., the top 3 recommendations.

In this way, the recommendation model may generate a probability, for each protocol group within each scanner model group, that the protocol group was applied to perform a scan of the selected procedure group, using the scanner model of the scanner model group and given the patient age and demographic information.

At 622, method 600 updates and sends the response. The response may be populated with the protocol group ID and usage counts for each scanner model group and recommended protocol group, as indicated at 624. For example, the model may identify five recommended protocol groups for a given scanner model group. For each of the five recommended protocol groups, the response may include the protocol group ID for that protocol group, the scanner model group, the confidence/probability of that protocol group, and usage counts for that protocol group. The usage counts may include the number of times in the past week the protocol group was executed, the number of times in the last month the protocol group was executed, and whether the protocol group was the last selected protocol group for that procedure group.

An example of a response to a protocol recommendation request is shown below (e.g., a response generated from the API request discussed above):

```
{
   "procedureGroup": [
      {
         "accesionNumber": "6235723",
         "procedureName": "CT HEAD"
      }
   ],
   "assignments": [
      {
         "scannerGroupId": "3fa85f64-5717-4562-b3fc-2c963f66af6"
         "recommendations": [
            {
               "protocolUUIDs": [
                  "PUUID1",
                  "PUUID2"
               ],
               "confidence": 100,
               "totalCount": 10,
               "countInLastWeek": 10,
               "countInLastMonth": 100,
               "lastSelected": true
            }
         ]
      }
   ]
}
```

Method 600 then returns.

In this way, prior scan protocols that were executed to scan prior patients for a variety of different procedures may be saved in a protocol-to-procedure mapping of a database of a core optimization system, where each protocol is mapped to one or more procedure groups. The database further stores the patient demographic data (e.g., age and BMI) and scanner model of each scan. When a request is received to generate a protocol recommendation for a given procedure or list of procedures, the protocol-to-procedure mapping may be queried to return a list of scan protocols, each of which are associated with the procedure or list of procedures. The request may further include patient demographic data for the patient to be scanned, and a recommendation model may be deployed to output a confidence score to each scan protocol of the list of scan protocols based on the patient demographic data. The list of scan protocols may then be sorted or grouped by scanner model group. The final list of scan protocols, sorted by scanner model group and including associated confidence scores, may then be sent to the device (e.g., computed tomography scanner) that initiated the request.

The recommendation model may be a statistical/classifier model (e.g., be a Gaussian Naïve Bayes model) that learns the confidence scores based on the probability that each scan protocol from the list of scan protocols will be selected to perform the scan, based on how frequently each scan protocol was selected historically for patients of similar demographics (e.g., similar age and BMI). In this way, the recommendation model only classifies scan protocols historically associated with the procedure or list of procedures and does not consider other scan protocols that may be saved on the protocol-to-procedure mapping (e.g., performed for other procedures), which may improve the efficiency of the recommendation model and hence the computing device (e.g., the core optimization system) executing the recommendation model.

Thus, the optimization engine/recommendation system disclosed herein may store and persist historical selections data along with associated patient demographic data and predict and recommend a scan level protocol for an imaging order based on the historical selection and patient demographic data.

The disclosed system leverages patient demographic information to identify suitable protocols for patient from the available list of protocols, the demographics used currently include age and BMI of the patient.

The disclosed system also leverages the past selection pattern of the user(s) as encountered by the system to align the suggested protocol recommendations with user behavior to improve the overall accuracy of the system.

The disclosed workflow/system creates a unique AI model for each unique procedure encountered, which restricts the classification problem to a smaller subset of possible historical behaviors which eradicates the possibility of cross procedure protocol recommendations.

The system does not require a pre-trained model to be trained on a specific sample data, rather the system encompasses the capability for the system to store and eventually learn post-deployment.

The disclosed system also proposes handling of missing values of patient demographic for protocol recommendation by replacing the missing values with 0 and allowing the classifier (e.g., model) to predict recommendations for inputs with missing data. Since the system removes the need to store a pre-built model, there is no overhead of model saving, update and management.

The system also adds the capability to segregate the learning based on scanner models, which enables unique or specific recommendation generation for each scanner model encountered in the learning by the system. For example, not all scanners have the same possible scan parameters available, and thus not all scanners may be equipped to carry out all protocols stored in the protocol library for a given imaging modality. By segregating the learning based on scanner models (e.g., the manufacturer of the scanner and the particular model type of the scanner), more accurate protocols may be recommended.

The classifier (e.g., model) may use a Gaussian Naïve Bayes classifier for the purpose of classification, which is fast for both training and inferencing, and is light weight with a small resource footprint.

The disclosed system can be scaled to implement an auto suggestion capability on the modality scanner (e.g., the CT scanner) where protocol recommendations can be auto-suggested for an incoming imaging order, so that the technologist can pick the scan level protocol from a pre-recommended list, thereby saving time. The disclosed system can also be scaled to implement an auto selection capability on the modality scanner where the most confident protocol recommendation is auto selected for an incoming imaging order.

A technical effect of recommending scan protocols is reduced cognitive load on radiologists and/or scan technicians and more accurately tailored scan protocols, thereby improving scan outcomes and lowering patient radiation dose and anxiety.

The disclosure also provides support for a method for a medical imaging system, the method comprising: receiving a request for a recommended scan protocol for a procedure of a scan to be performed on a patient using the medical imaging system, identifying one or more scan protocols for conducting the scan based on prior scan protocols performed for the procedure and patient demographic data of the patient, and outputting the one or more scan protocols for display on a display device and/or automatically executing the one or more scan protocols. In a first example of the method, identifying the one or more scan protocols comprises extracting a plurality of scan protocols from a protocol-to-procedure mapping stored in a database based on the procedure and generating a confidence level of each scan protocol of the plurality of scan protocols with a recommendation model. In a second example of the method, optionally including the first example, the method further comprises: entering, as input to the recommendation model, the plurality of scan protocols extracted from the database and a query vector, the query vector including the patient demographic data. In a third example of the method, optionally including one or both of the first and second examples, the recommendation model comprises a Gaussian Naïve Bayes model. In a fourth example of the method, optionally including one or more or each of the first through third examples, the protocol-to-procedure mapping includes the plurality of scan protocols mapped to the procedure, the plurality of scan protocols comprising the prior scan protocols performed for the procedure. In a fifth example of the method, optionally including one or more or each of the first through fourth examples, the database further stores respective patient demographic data and a respective scanner model for each of the plurality of scan protocols. In a sixth example of the method, optionally including one or more or each of the first through fifth examples, the protocol-to-procedure mapping further includes additional scan protocols mapped to additional procedures. In a seventh example of the method, optionally including one or more or each of the first through sixth examples, the patient demographic data comprises patient age and patient body mass index.

The disclosure also provides support for a method, comprising: receiving, from a client device, a scan protocol recommendation request including a list of procedures to be performed during scan of a patient, generating a procedure group from the list of procedures, determining that the procedure group exists in a protocol-to-procedure mapping stored in a database, and in response, extracting all entries from the database associated with the procedure group, creating a dictionary from the extracted entries, the dictionary including one or more scanner model groups and one or more scan protocols for each scanner model group, applying a classifier model to the dictionary with a query vector of patient demographic information, and sending, to the client device, a list of recommended scan protocols based on output of the classifier model. In a first example of the method, the method further comprises: receiving, from the client device, an indication of one or more scan protocols that were executed during the scan of the patient, and in response, saving a respective identifier for the one or more scan protocols in the protocol-to-procedure mapping of the database. In a second example of the method, optionally including the first example, the method further comprises: receiving, from the client device, a second scan protocol recommendation request including a second list of procedures to be performed during second scan of a second patient, generating a second procedure group from the second list of procedures, and determining that the second procedure group does not exist in the protocol-to-procedure mapping, and in response, sending a notification to the client device that a recommended scan protocol is not available. In a third example of the method, optionally including one or both of the first and second examples, the classifier model outputs a confidence score for each of the one or more scan protocols for each scanner model group based on the patient demographic information. In a fourth example of the method, optionally including one or more or each of the first through third examples, the patient demographic information comprises patient age and patient body mass index. In a fifth example of the method, optionally including one or more or each of the first through fourth examples, the method further comprises: determining that the patient age or the patient body mass index is not available, and in response, entering a value of zero for the patient age or the patient body mass index. In a sixth example of the method, optionally including one or more or each of the first through fifth examples, the classifier model is a Gaussian Naïve Bayes model.

The disclosure also provides support for a system, comprising: a core optimization system, a database, and a client device, where the core optimization system includes instructions stored in memory that are executable to: populate the database with protocol-to-procedure mappings determined based on data received from the client device, generate a list of recommended scan protocols based on the protocol-to-procedure mappings in response to receiving a recommendation request from the client device, the recommendation request including a list of procedures to be performed in a scan of a patient and demographic data of the patient, and send the list of recommended scan protocols to the client device. In a first example of the system, the instructions are executable to enter a list of protocol groups identified by the protocol-to-procedure mappings and the demographic data of the patient into a classifier model trained to output a confidence score for each protocol group based on the demographic data of the patient. In a second example of the system, optionally including the first example, the list of recommended scan protocols comprises the list of protocol groups and associated confidence scores. In a third example of the system, optionally including one or both of the first and second examples, the list of protocol groups is identified based on the list of procedures. In a fourth example of the system, optionally including one or more or each of the first through third examples, the client device comprises a computed tomography scanner.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a medical imaging system, the method comprising:
   receiving a request for a recommended scan protocol for a procedure of a scan to be performed on a patient using the medical imaging system;
   identifying one or more scan protocols for conducting the scan based on prior scan protocols performed for the procedure and patient demographic data of the patient, wherein identifying the one or more scan protocols comprises extracting a plurality of scan protocols from a protocol-to-procedure mapping stored in a database based on the procedure and generating a confidence level of each scan protocol of the plurality of scan protocols with a recommendation model; and
   outputting the one or more scan protocols for display on a display device and/or automatically executing the one or more scan protocols.

2. The method of claim 1, further comprising entering, as input to the recommendation model, the plurality of scan protocols extracted from the database and a query vector, the query vector including the patient demographic data.

3. The method of claim 2, wherein the recommendation model comprises a Gaussian Naïve Bayes model.

4. The method of claim 1, wherein the protocol-to-procedure mapping includes the plurality of scan protocols mapped to the procedure, the plurality of scan protocols comprising the prior scan protocols performed for the procedure.

5. The method of claim 4, wherein the database further stores respective patient demographic data and a respective scanner model for each of the plurality of scan protocols.

6. The method of claim 4, wherein the protocol-to-procedure mapping further includes additional scan protocols mapped to additional procedures.

7. The method of claim 1, wherein the patient demographic data comprises patient age and patient body mass index.

8. A method, comprising:
   receiving, from a client device, a scan protocol recommendation request including a list of procedures to be performed during scan of a patient;
   generating a procedure group from the list of procedures;
   determining that the procedure group exists in a protocol-to-procedure mapping stored in a database, and in response, extracting all entries from the database associated with the procedure group;
   creating a dictionary from the extracted entries, the dictionary including one or more scanner model groups and one or more scan protocols for each scanner model group;
   applying a classifier model to the dictionary with a query vector of patient demographic information; and
   sending, to the client device, a list of recommended scan protocols based on output of the classifier model.

9. The method of claim 8, further comprising receiving, from the client device, an indication of one or more scan protocols that were executed during the scan of the patient, and in response, saving a respective identifier for the one or more scan protocols in the protocol-to-procedure mapping of the database.

10. The method of claim 8, further comprising receiving, from the client device, a second scan protocol recommendation request including a second list of procedures to be performed during second scan of a second patient;
    generating a second procedure group from the second list of procedures; and
    determining that the second procedure group does not exist in the protocol-to-procedure mapping, and in response, sending a notification to the client device that a recommended scan protocol is not available.

11. The method of claim 8, wherein the classifier model outputs a confidence score for each of the one or more scan protocols for each scanner model group based on the patient demographic information.

12. The method of claim 11, wherein the patient demographic information comprises patient age and patient body mass index.

13. The method of claim 12, further comprising determining that the patient age or the patient body mass index is not available, and in response, entering a value of zero for the patient age or the patient body mass index.

14. The method of claim 12, wherein the classifier model is a Gaussian Naïve Bayes model.

15. A system, comprising:
    a core optimization system;
    a database; and
    a client device, where the core optimization system includes instructions stored in memory that are executable to:
       populate the database with protocol-to-procedure mappings determined based on data received from the client device;
       generate a list of recommended scan protocols based on the protocol-to-procedure mappings in response to receiving a recommendation request from the client device, the recommendation request including a list of procedures to be performed in a scan of a patient and demographic data of the patient; and
       send the list of recommended scan protocols to the client device.

16. The system of claim 15, wherein the instructions are executable to enter a list of protocol groups identified by the protocol-to-procedure mappings and the demographic data of the patient into a classifier model trained to output a confidence score for each protocol group based on the demographic data of the patient.

17. The system of claim 16, wherein the list of recommended scan protocols comprises the list of protocol groups and associated confidence scores.

18. The system of claim 16, wherein the list of protocol groups is identified based on the list of procedures.

19. The system of claim 15, wherein the client device comprises a computed tomography scanner.

* * * * *